US007319112B2

(12) United States Patent
Haught et al.

(10) Patent No.: US 7,319,112 B2
(45) Date of Patent: Jan. 15, 2008

(54) NON-HALOGENATED ANTIBACTERIAL AGENTS AND PROCESSES FOR MAKING SAME

(75) Inventors: John Christian Haught, West Chester, OH (US); Gregory Scot Miracle, Hamilton, OH (US); Andre Christian Convents, Diegem (BE); George Douglas Hiler, II, Harrison, OH (US); David Johnathan Kitko, Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 737 days.

(21) Appl. No.: 10/662,644

(22) Filed: Sep. 15, 2003

(65) Prior Publication Data

US 2004/0072908 A1    Apr. 15, 2004

Related U.S. Application Data

(63) Continuation-in-part of application No. 09/903,309, filed on Jul. 11, 2001, now abandoned.

(60) Provisional application No. 60/411,812, filed on Sep. 18, 2002, provisional application No. 60/218,207, filed on Jul. 14, 2000.

(51) Int. Cl.
*A01N 37/18* (2006.01)
(52) U.S. Cl. .................. 514/617; 514/618; 514/619
(58) Field of Classification Search .............. 544/1; 514/617, 618, 619
See application file for complete search history.

(56) References Cited

U.S. PATENT DOCUMENTS

| | | | |
|---|---|---|---|
| 2,092,300 A | 9/1937 | Bogin | |
| 2,906,711 A | 9/1959 | Stecker et al. | |
| 3,041,236 A | 6/1962 | Stecker et al. | |
| 3,256,200 A | 6/1966 | William | |
| 3,311,562 A | 3/1967 | Stecker | |
| 3,321,524 A | 5/1967 | Harich | |
| 3,594,322 A | 7/1971 | Wilson | |
| 3,664,961 A | 5/1972 | Norris | |
| 3,666,668 A | 5/1972 | Klausner et al. | |
| 3,666,808 A | 5/1972 | Meek | |
| 3,968,210 A | 7/1976 | Schenkel et al. | |
| 3,989,827 A | 11/1976 | Apostolatos et al. | |
| 4,008,274 A | 2/1977 | Sawatari et al. | |
| 4,061,603 A | 12/1977 | Rubinfeld et al. | |
| 4,287,191 A | 9/1981 | Coburn et al. | |
| 4,358,443 A | 11/1982 | Coburn et al. | |
| 4,560,549 A | 12/1985 | Ritchey et al. | |
| 4,647,452 A | 3/1987 | Ritchey et al. | |
| 4,725,590 A | 2/1988 | Ritchey et al. | |
| 4,742,083 A | 5/1988 | Ritchey et al. | |
| 4,939,132 A | 7/1990 | Coburn et al. | |
| 5,342,437 A | 8/1994 | Gavin | |
| 5,576,282 A | 11/1996 | Miracle et al. | |
| 5,605,832 A | 2/1997 | Damhus et al. | |
| 5,646,101 A | 7/1997 | MacBeath | |
| 5,683,654 A | 11/1997 | Dallmier et al. | |
| 5,686,014 A | 11/1997 | Baillely et al. | |
| 5,695,679 A | 12/1997 | Christie et al. | |
| 5,698,504 A | 12/1997 | Christie et al. | |
| 5,705,464 A | 1/1998 | Scheper et al. | |
| 5,707,950 A | 1/1998 | Kasturi et al. | |
| 5,710,115 A | 1/1998 | Patel et al. | |
| 5,728,671 A | 3/1998 | Rohrbaugh et al. | |
| 5,919,152 A | 7/1999 | Zygmont et al. | |
| 5,958,911 A | 9/1999 | Evans et al. | |
| 6,017,871 A | 1/2000 | Baeck et al. | |
| 6,117,859 A | 9/2000 | Evans et al. | |
| 2002/0068014 A1 | 6/2002 | Haught et al. | |

FOREIGN PATENT DOCUMENTS

| | | |
|---|---|---|
| BE | 528076 | 1/1957 |
| CH | 449571 | 9/1967 |
| CH | 500 661 | 2/1971 |
| DE | 2157209 | 5/1973 |
| DE | 4428380 A1 | 2/1996 |
| DE | 195 23389 A1 | 1/1997 |
| DE | 196 12193 A1 | 10/1997 |
| EP | 0 698 659 A1 | 2/1996 |
| EP | 0 709 452 A1 | 5/1996 |
| EP | 0 747 470 A1 | 12/1996 |
| EP | 0 747469 A1 | 12/1996 |
| FR | 1071945 | 9/1954 |
| FR | 500661 | 12/1970 |
| GB | 848306 | 9/1960 |
| GB | 2 294 269 A | 4/1996 |

(Continued)

OTHER PUBLICATIONS

Brown et al (Synthesis of Benzoylsalicylanilides, J. Med. Chem., 1985,28,143-146).*

(Continued)

*Primary Examiner*—Alton Pryor
(74) *Attorney, Agent, or Firm*—James F. McBride

(57) ABSTRACT

The present invention provides antibacterial compounds, antibacterial compositions, bacteria-reducing methods, bacteria-reduced substrates/articles made by the methods that employ an antibacterial agent comprising a non-halogenated nitrile-substituted salicylanilide, and processes for producing 5-acyl salicylamides.

5 Claims, No Drawings

FOREIGN PATENT DOCUMENTS

| | | |
|---|---|---|
| GB | 2 297 979 A | 8/1996 |
| GB | 2 303 147 A | 2/1997 |
| JP | 57-142903 | 9/1982 |
| JP | 09316490 A | 12/1997 |
| JP | 10088472 A | 4/1998 |
| JP | 10088485 A | 4/1998 |
| JP | 10174583 A | 6/1998 |
| WO | WO 95/26397 A1 | 10/1995 |
| WO | WO 95/35382 A2 | 12/1995 |
| WO | WO 96/12004 A1 | 4/1996 |
| WO | WO 96/16153 A1 | 5/1996 |
| WO | WO 96/16154 A1 | 5/1996 |
| WO | WO 96/23873 A1 | 8/1996 |
| WO | WO 96/27649 A1 | 9/1996 |
| WO | WO 96/28558 A1 | 9/1996 |
| WO | WO 97/08325 A1 | 3/1997 |
| WO | WO 97/09431 A1 | 3/1997 |
| WO | WO 97/11164 A1 | 3/1997 |
| WO | WO 97/11217 A1 | 3/1997 |
| WO | WO 97/25468 A1 | 7/1997 |
| WO | WO 97/25469 A1 | 7/1997 |
| WO | WO 97/28257 A1 | 8/1997 |
| WO | WO 97/31090 A1 | 8/1997 |
| WO | WO 97/40127 A1 | 10/1997 |
| WO | WO 97/40229 A1 | 10/1997 |
| WO | WO 98/06805 A1 | 2/1998 |
| WO | WO 98/06807 A1 | 2/1998 |
| WO | WO 98/06808 A1 | 2/1998 |
| WO | WO 98/06809 A1 | 2/1998 |
| WO | WO 98/07816 A1 | 2/1998 |
| WO | WO 98/10060 A1 | 3/1998 |
| WO | WO 98/13457 A1 | 4/1998 |
| WO | WO 98/15633 A1 | 4/1998 |
| WO | WO 98/16604 A2 | 4/1998 |
| WO | WO 98/24800 A2 | 6/1998 |
| WO | WO 98/27197 A1 | 6/1998 |
| WO | WO 98/27198 A1 | 6/1998 |
| WO | WO 98/28394 A1 | 7/1998 |
| WO | WO 98/38286 A1 | 9/1998 |
| WO | WO 98/38287 A1 | 9/1998 |
| WO | WO 98/39402 A1 | 9/1998 |
| WO | WO 98/39403 A1 | 9/1998 |
| WO | WO 98/39404 A1 | 9/1998 |
| WO | WO 98/40473 A1 | 9/1998 |
| WO | WO 98/50513 A1 | 11/1998 |
| WO | WO 99/02663 A1 | 1/1999 |
| WO | WO 99/09126 A1 | 2/1999 |
| WO | WO 01/60157 A2 | 8/2001 |
| WO | WO 02/28819 A1 | 4/2002 |

OTHER PUBLICATIONS

Natarajan et al., 1992, Indian Drugs 29:545-552.
Lemair et al., 1961 J. Pharmaceutical Sciences, 50:831-837.
Ciampa G. et al. "N-Substituted salicylanilides. I. Halogenated 2-hydroxy- and 2-acetoxybenanilides with antibacterial and antifungal activity" vol. 68, No. 21, 6001 Chemical Abstracts, Columbus, OH, USA XP002177845 ISSN: 0009-2258 abstract.
Abstract XP 002177846 equivalent to abstract for cite 117.
Smith et al. Fungitoxic derivatives of salicyladehyde, 1961, Ann. Appl. Biol. vol. 49, pp. 102-109.
Gurevich, E. S. et al. "Use of org. poisons in antifouling paints" retrieved from STN Database accession No. 5293a XP002191164 & Chemical Abstracts, vol. 64, No. 4, Feb. 14, 1966.
Hoffman, Erich et al. "Formulation of fungus-resistant paints. V. Addition of saliclanilide" retrieved from STN Database accession No. 71:51292 XP002191175 abstract & J. Oil Colour Chem. Ass. (1969), 52(7).
George R. Brown, et al. Potentiation of Fasciolicidal Agents by Benzoyl Side Chains. Journal of Medicinal Chemistry, vol. 28, 1985, pp. 143-146.
J. H. Amin, The Fries Reaction, part IV-The Rearrangement of the Derivatives of Salicylic Acid & Substituted Benzoic Acids, Scientific & Industrial Research, vol. 138, No. 1, 1954, pp. 178-179.
Truong, Phuong et al. "Synthesis and biological properties of chorosalicylamide derivatives" retrieved from STN Database accession No. 129:230511 XP 002191176 abstract & TAP CHI DUOC HOC (1998) (5) 8-12.

\* cited by examiner

NON-HALOGENATED ANTIBACTERIAL AGENTS AND PROCESSES FOR MAKING SAME

CROSS-REFERENCES TO RELATED APPLICATIONS

This application is a continuation-in-part of U.S. application Ser. No. 09/903,309, filed Jul. 11, 2001, now abandoned which in turn claims priority to U.S. Provisional Application Ser. No. 60/218,207 filed Jul. 14, 2000. This application also claims priority under 35 U.S.C. 0 119(e) to U.S. Provisional Application Ser. No. 60/411,812 filed Sep. 18, 2002. U.S. application Ser. No. 09/903,309 and U.S. Provisional Application Ser. No. 60/411,812 are herein incorporated by reference.

FIELD OF THE INVENTION

The present invention relates to non-halogenated salicylanilide antibacterial agents, more particularly nitrile-substituted salicylanilide compositions, and methods of producing 5-acyl salicylamides and using same.

BACKGROUND OF THE INVENTION

Consumers and retail establishments are very conscientious about cleanliness and/or sanitization, especially when it comes to dishes, utensils, tableware, cookware, cleaning articles that are typically found and/or used in kitchens and bathrooms, textiles, fabrics and garments. Thus, there is a need for a compositions and methods that sanitize such articles.

Although multi-halogenated salicylanilides are effective antibacterials when used in a detergent matrix, these compounds have not enjoyed widespread use due to a variety of reasons, including but not limited to problems encountered in formulating these agents. Moreover, such halogenated salicylanilides often give rise to increased concerns regarding human and environmental safety. Applicants recognized that such drawbacks are rooted in the halogenation of salicylanilides and that, if properly synthesized and employed, non-halogenated salicylanilides can be effective antibacterials. Accordingly there remains a need for non-halogenated salicylanilides that are effective antibacterials and a means of economically synthezing and using such compounds.

SUMMARY OF THE INVENTION

The present invention provides antibacterial compounds, antibacterial compositions, bacteria-reducing methods, bacteria-reduced substrates/articles made by the methods that employ an antibacterial agent comprising a non-halogenated nitrile-substituted salicylanilide, and processes for producing 5-acyl salicylamides.

All percentages, ratios and proportions herein are on a weight basis based on a neat product unless otherwise indicated. All documents cited herein are hereby incorporated by reference.

DETAILED DESCRIPTION OF THE INVENTION

Definitions

As used herein, "substituted" means that the organic composition or radical to which the term is applied is:

(a) made unsaturated by the elimination of elements or radical; or (b) at least one hydrogen in the compound or radical is replaced with a moiety containing one or more (i) carbon, (ii) oxygen, (iii) sulfur, or (iv) nitrogen atoms; or (c) both (a) and (b).

Moieties which may replace hydrogen as described in (b) immediately above, that contain only carbon and hydrogen atoms are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups.

It is understood that any of the above moieties (b)(i) through (b)(iv) can be substituted into each other in either a monovalent substitution or by loss of hydrogen in a polyvalent substitution to form another monovalent moiety that can replace hydrogen in the organic compound or radical.

As used herein, the term "perfume" means a fragrance raw material or mixture of fragrance raw materials that impart a scent, odor, essence, or fragrance characteristic.

As used herein, "fragrance raw materials" are compounds having a molecular weight of at least 100 g/mol and are useful in imparting an odor, fragrance, essence, or scent either alone or in combination with other "fragrance raw materials".

As used herein, the C log P of a perfume, (C log P)$_p$, is calculated as the weighted average of the C log P values of the n individual fragrance raw materials, (C log P)$_i$, that comprise the perfume, according to the formula:

$$(\text{C}\log P)_p = \sum_{i=1}^{n}\left(\frac{w_i}{w_p}\right)(\text{C}\log P)_i$$

wherein $w_i$ is the weight of the nth fragrance raw material and $w_p$, the weight of the perfume, is the sum of the weights of the n individual fragrance raw materials according to the formula:

$$w_p = \sum_{i=1}^{n} w_i$$

All fragrance raw materials present in an amount such that $(w_i/w_p)>0.01$ constitute the n fragrance raw materials of the perfume for the purpose of determining $(C \log P)_p$.

Antibacterial Composition

The composition of the present invention comprises a non-halogenated nitrile-substituted salicylanilide compound of formula I.

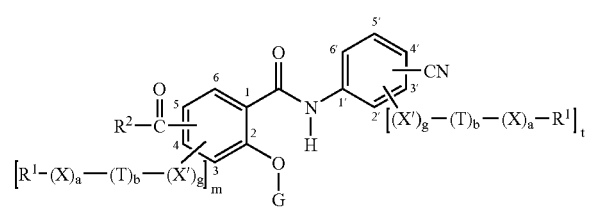

I

Wherein:
a.) m is an integer from 0 to 3;
b.) t is an integer from 0 to 4;
c.) a is 0 or 1;
d.) b is 0 or 1;
e.) g is 0 or 1;
f.) $R^1$ for said radical is independently selected from the group consisting of:
  i) H;
  ii) $C_1$-$C_{16}$ linear or branched, substituted or unsubstituted alkyl;
  iii) $C_2$-$C_{16}$ linear or branched, substituted or unsubstituted alkenyl;
  iv) $C_2$-$C_{16}$ linear or branched, substituted or unsubstituted alkynyl;
  v) $C_3$-$C_{16}$ linear or branched, substituted or unsubstituted cycloalkyl;
  vi) $C_3$-$C_{16}$ linear or branched, substituted or unsubstituted cycloalkenyl;
  vii) $C_7$-$C_{16}$ linear or branched, substituted or unsubstituted alkaryl;
  viii) $C_7$-$C_{16}$ linear or branched, substituted or unsubstituted aralkyl;
  ix) $C_6$-$C_{16}$ substituted or unsubstituted aryl;
  x) $C_5$-$C_{20}$ heteroaryl units comprising one or more heteroatoms selected from the group consisting of nitrogen, oxygen, sulfur, and mixtures thereof; and
  xi) a suitable charge balancing counterion $(M^{n+})_{1/n}$, provided a and b are both 1 and X is selected from O and S;
  xii) when a, b and g are all 0 for any single radical, $R^1\text{---}(X)_a\text{-}(T)_b\text{-}(X')_g\text{---}$, $R^1$ for said radical may be further selected from the group consisting of CN, an amine oxide moiety, $NO_2$ and mixtures thereof;
g.) X and X', when present, are selected from O, S, and $NR^2$;
h.) each $R^2$ is independently selected from the group consisting of:
  i) H;
  ii) $C_1$-$C_{16}$ linear or branched, substituted or unsubstituted alkyl;
  iii) $C_2$-$C_{16}$ linear or branched, substituted or unsubstituted alkenyl;
  iv) $C_2$-$C_{16}$ linear or branched, substituted or unsubstituted alkynyl;
  v) $C_3$-$C_{16}$ linear or branched, substituted or unsubstituted cycloalkyl;
  vi) $C_3$-$C_{16}$ linear or branched, substituted or unsubstituted cycloalkenyl;
  vii) $C_7$-$C_{16}$ linear or branched, substituted or unsubstituted alkaryl;
  viii) $C_7$-$C_{16}$ linear or branched, substituted or unsubstituted aralkyl;
  ix) $C_6$-$C_{16}$ substituted or unsubstituted aryl; and
  x) $C_5$-$C_{20}$ heteroaryl units comprising one or more heteroatoms selected from the group consisting of nitrogen, oxygen, sulfur, and mixtures thereof;
i.) T, when present, is selected from C=O, C=S, S=O, and $SO_2$; when T is S=O or $SO_2$, X and X' associated with said T may not be S;
j.) G is:
  i) H;
  ii) a suitable charge balancing counterion $(M^{n+})_{1/n}$, or
  iii) a cleaveable group selected from the group consisting of $Si((O)_p R^3)_3$, where p is independently 0 or 1; $C(O)_q((O)_p R^3)_r$, wherein p is independently 0 or 1 and when q is 1, r is 1, and when q is 0, r is 3; $R^3$ is independently selected from the group consisting of $C_1$-$C_{16}$ linear or branched, substituted or unsubstituted alkyl, alkenyl, alkynyl, cycloalkyl, cycloalkenyl, alkaryl, aralkyl, and aryl, and mixtures thereof provided that when, for any radical, b is 0, a, g, or a and g are 0 for said radical.

In one embodiment of the present invention, the composition comprises at least one additional component selected from the group consisting of:
  a) a surfactant wherein either:
    (i) the ratio of the weight of the surfactant divided by the weight of the substituted salicylanilide compound of formula I is greater than or equal to 1.0 and further provided that the surfactant is 1 wt % or greater of the composition; or
    (ii) the composition comprises at least 1 wt % of a cationic surfactant, wherein the ratio of the weight of the surfactant divided by the weight of said compound I is greater than or equal to 1.0; and wherein a 10 wt % aqueous solution of this composition has a pH less than or equal to 7.0;
  b) from 0.5% to 90% by weight of a solvent said solvent having Hildebrand solubility parameter $d_S$ $(cal/cm^3)^{1/2}$ meeting the following criterion: $5<d_S<20$, wherein a 10 wt % aqueous solution of this composition has a $pH \geq (pKa-1)$ where pKa is the calculated pKa of the O-G phenol of formula I, or when G is not H, the pKa of the O-G phenol of formula I that results from replacing G with H;
  c) a perfume having a C log P greater than or equal to 2.0;
  d) 0.001 to 1.0% by weight of an enzyme; and
  e) mixtures thereof.

In another aspect of the invention, the enzyme is selected from the group consisting of: proteases, amylases, cellulases, mannanases, xyloglucanases, pectinases, lipases, laccases, peroxidases and mixtures thereof.

In another aspect of the invention, the composition comprises at least two of said additional components.

In another aspect of the invention, the composition comprises a liquid detergent.

In another aspect of the invention, the composition comprises a compound of Formula I above wherein m is 0 or 1; t is 0 or 1; a, b and g are all 0; G is H and $R^1$, when present, is not H.

In another aspect of the invention, the composition comprises a compound of Formula I above wherein m is 0 or 1; t is 0 or 1; and G is H.

In another aspect of the invention, the composition comprises a compound of Formula I above wherein m is 0 or 1; t is 0; and G is H.

In another aspect of the invention, the composition comprises a compound of Formula I above wherein m is 0 or 1; t is 0; all a, b and g are 0, and G is H.

In another aspect of the invention, the composition comprises a compound of Formula I above wherein m is 0; t is 0; all a, b and g are 0, and G is H.

In another aspect of the invention the composition comprises a compound selected from the group consisting of Formula II, Formula III or mixtures thereof:

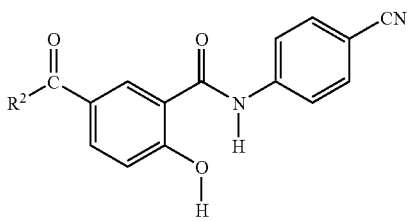

Formula II

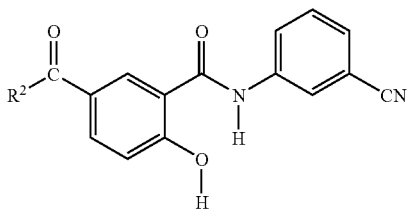

Formula III wherein $R^2$ for Formula II and Formula III is selected from the group consisting of:
i) H;
ii) $C_1$-$C_{16}$ linear or branched, substituted or unsubstituted alkyl;
iii) $C_2$-$C_{16}$ linear or branched, substituted or unsubstituted alkenyl;
iv) $C_2$-$C_{16}$ linear or branched, substituted or unsubstituted alkynyl;
v) $C_3$-$C_{16}$ linear or branched, substituted or unsubstituted cycloalkyl;
vi) $C_3$-$C_{16}$ linear or branched, substituted or unsubstituted cycloalkenyl;
vii) $C_7$-$C_{16}$ linear or branched, substituted or unsubstituted alkaryl;
viii) $C_7$-$C_{16}$ linear or branched, substituted or unsubstituted aralkyl;
ix) $C_6$-$C_{16}$ substituted or unsubstituted aryl; and
x) $C_5$-$C_{20}$ heteroaryl units comprising one or more heteroatoms selected from the group consisting of nitrogen, oxygen, sulfur, and mixtures thereof.

In another aspect of the invention the composition comprises a compound of Formula II, Formula III or mixtures thereof wherein $R^2$ is selected from the group consisting of $C_1$-$C_{16}$ linear or branched, substituted or unsubstituted alkyl; and $C_6$-$C_{16}$ substituted or unsubstituted aryl.

Suitable surfactants for use in the compositions disclosed herein include, but are not limited to, nonionic, anionic, amphoteric, amphophilic, zwitterionic, cationic, semi-polar nonionic, and mixtures thereof. Non-limiting examples of such surfactants are disclosed in U.S. Pat. Nos. 3,664,961, 5,707,950 and 5,576,282. In one aspect of the present invention said compositions comprise nonionic surfactants and/or mixtures of nonionic surfactants with other surfactants, especially anionic surfactants. Specific examples of suitable surfactants include, but are not limited to, linear alkylbenzene sulfonate, sodium salt (Sodium LAS), available from Huntsman Surface Sciences, 3040 Post Oak Boulevard, Houston, Tex. U.S.A. 77056; Neodol 25-9®, available from Shell Chemical LP, PO Box 2463, Houston, Tex. U.S.A. 77252; Dimethyl hydroxyethyl lauryl ammonium chloride, available from Clariant Corporation, 4331 Chesapeake Drive, Charlotte, N.C. U.S.A. 28216.

Suitable perfumes include, but are not limited to fragrance raw materials that typically comprise alcohols, ketones, aldehydes, esters, ethers, nitriles, and cyclic and acyclic alkenes such as terpenes. Examples of fragrance raw materials that are useful in the compositions of the present invention include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma. Such fragrance raw material can be obtained from IFF Global Headquarters, 521 West 57th Street, New York, N.Y. U.S.A 10019.

Suitable solvents for incorporation in the compositions of the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. Water-soluble CELLOSOLVE® solvents are compounds of the 2-alkoxyethoxyethanol class, such as 2-butoxyethoxyethanol. Other suitable solvents include ethanolamines and alcohols such as n-butoxypropoxypropanol, butyl carbitol®, monoethanolamine (MEA), diethanolamine, triethanolamine, benzyl alcohol, methanol, ethanol, isopropyl alcohol and diols such as 2-ethyl-1,3-hexanediol and 2,2,4-trimethyl-1,3-pentanediol and mixtures thereof. Suitable solvents such as CARBITOL® solvents or water-soluble CELLOSOLVE® can be obtained from The Dow Chemical Company, 40 Veronica Avenue, Somerset, N.J. U.S.A. 08873.

Other useful solvents for use in the present compositions include a poly(alkylene glycol)alkyl ethers. Suitable poly(alkylene glycol)alkyl ethers for use herein include poly (propylene glycol) mono butyl ether, poly(ethylene glycol-co-propylene glycol) mono butyl ether, poly(ethylene glycol)dimethyl ether, poly(ethylene glycol-co-propylene glycol)dimethyl ether, poly(ethylene glycol)stearate or mixtures thereof. Poly(propylene glycol)mono butyl ether (average molecular weight 340) is commercially available from Aldrich, P.O. Box 2060, Milwaukee, Wis. U.S.A. 53201.

Other useful solvents for use in the present compositions include non-aqueous, low-polarity solvents such as the non-vicinal $C_4$-$C_8$ branched or straight chain alkylene glycols. Solvents of this type include hexylene glycol (4-methyl-2,4-pentanediol), 1,6-hexanediol, 1,3-butylene glycol and 1,4-butylene glycol. Other low-polarity solvent for use herein comprises the mono-, di-, tri-, or tetra-$C_2$-$C_3$ alkylene glycol mono $C_2$-$C_6$ alkyl ethers. Non-limiting examples of such compounds include diethylene glycol monobutyl ether, tetraethylene glycol monobutyl ether, dipropolyene glycol monoethyl ether, and dipropylene glycol monobutyl ether.

Another solvent useful herein comprises the lower molecular weight polyethylene glycols (PEGs). Such materials are those having molecular weights of at least about 150 grams/mole.

Suitable enzymes for incorporation in the compositions of the present invention include, but are not limited to, chondriotinase, hemicellulases, endoglucanase, peroxidases, proteases, pectolyase, cellulases, xylanases, lipases, phospholipases, esterases, cutinases, isopeptidase, pectinases, pectin lyases free from other pectic enzymes, keratanases, reductases, oxidases, oxidoreductases, phenoloxidases, lipoxygenases, ligninases, pullulanases, tannases, pentosanases, malanases, β-glucanases, arabinosidases, hyaluronidase, chondroitinase, laccase, mannanases, xylanase, keratinase, polygalacturonase, mycodextranase, thermitase, amylases, xyloglucanases, laccases, superoxide dismutases, catalases. Examples of these and other such suitable enzymes and/or levels of use are disclosed in WO 98/28400 A2; WO 98/39403 A; WO 98/06808 A; WO 98/06805 A1; WO 98/06807 A1; WO 98/39404 A; WO 98/39402 A; WO 98/16604 A; WO 98/40473 A; WO 96/16153 A; WO 96/12004 A; WO 96/16154 A; WO 96/27649 A; WO 98/03640 A; WO 98/15633 A; WO 98/06809 A; WO 98/13457 A; WO 96/28558 A; WO 98/28394 A; WO 97/09431 A1; WO 97/31090 A1; WO 97/11164; WO 99/09126; WO 98/50513; WO 99/02663; WO 98/38287 A1; WO 98/38286 A1; WO 98/27197 A1; WO 98/10060 A1; WO 98/27198 A1; WO 97/11217 A; WO 97/25468 A; WO 97/25469 A; WO 97/40127 A1; WO 97/40229 A1; WO 97/08325 A; WO 97/28257 A1; WO 98/07816 A.; EP 747,469 A; EP 709,452 A; EP 747,470 A; EP 698,659 A; GB 2,297,979 A; GB 2,294,269 A; GB 2,303,147 A; DE 19523389 A1; DE/19612193 A1; JP 09316490 A; JP 10088472 A; JP10088485 A; JP 10174583 A; and U.S. Pat. Nos. 5,705,464; 5,710,115; 5,576,282; 5,728,671; 5,707,950; 5,605,832; and 5,683,911.

Examples of commercial α-amylases products are Purafect Ox Am® from Genencor and Termamyl®, Ban®, Fungamyl® and Duramyl®, all available from Novo Nordisk A/S Denmark. WO 95/26397 describes other suitable amylases: α-amylases characterized by having a specific activity at least 25% higher than the specific activity of Termamyl® at a temperature range of 25° C. to 55° C. and at a pH value in the range of 8 to 10, measured by the Phadebas® α-amylase activity assay. Suitable are variants of the above enzymes, described in WO 96/23873 (Novo Nordisk). Other amylolytic enzymes with improved properties with respect to the activity level and the combination of thermostability and a higher activity level are described in WO 95/35382. Enzyme selection is influenced by factors such as pH-activity and/or stability optima, thermostability, and stability to active detergents, builders and the like.

The compositions of the present invention may comprise suitable adjunct ingredients including, but not limited to, builders, bleaches, bleach activators, bleach catalysts, catalytic metal complexes, enzyme stabilizing systems, chelants, optical brighteners, soil release polymers, dye transfer agents, dispersants, suds suppressors, dyes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments and pH control agents as described in U.S. Pat. Nos. 5,705,464, 5,710,115, 5,698,504, 5,695,679, 5,686,014 and 5,646,101. A sufficient number and amount of such adjunct ingredients may be added to form a cleaning or other consumer composition, including but not limited to, liquid detergent compositions, heavy duty detergent compositions, automatic or hand dishwashing compositions, hard surface cleaning compositions, home care compositions, fabric care compositions and dryer-added compositions.

The compositions and compounds of the present invention can be incorporated into or include a range of different products including, but not limited to, liquid detergent compositions, heavy duty detergent compositions, automatic or hand dishwashing compositions, hard surface cleaning compositions, home care compositions, fabric care compositions and dryer-added compositions. These products may be in any form known to those skilled in the art and the compounds and compositions of the present invetion may be incorporated into such detergents by conventional means including but not limited to simple mixing. For example, the products may be in liquid, granular, powder, tablet, paste, foam, gel, spray and bars. These products may be neat or releasably absorbed or adsorbed on to a substrate, such as a woven or non-woven filament substrate.

When bacteria are contacted with the compositions disclosed herein and/or the compounds having Formulae I-V, for the bacteria are reduced and/or their growth is inhibited. Examples of bacteria that can be reduced and/or whose growth is inhibited by contact with the compositions disclosed herein and/or the compound having Formulae I-V include, but are not limited to, *Staphylococcus aureus, Staphylococcus haemolyticus, Staphylococcus capitis, Staphylococcus saprophyticus, Klebsiella pneumoniae, Proteus mirabilis, Bacillus thuringiensis; Serratia marcescens, Staphylococcus epidermidis, Salmonella typhimurium, Shigella dysenteriae, Streptococcus faecalis, Streptococcus pyogenes, Corynebacterium xerosis, Micrococcus varians, Micrococcus luteus, Peptostreptococcus anaerobius, Propionibacterium acnes, Propionibacterium avidum, Propionibacterium granulosum, Escherichia coli, Salmonella choleraesius, Listeria monocytogenes, Enterococcus hirae* and mixtures thereof. In one aspect of Applicants' invention, bacteria that can be reduced and/or whose growth is inhibited by contact with the compositions disclosed herein and/or the compound having Formulae I-V include, but are not limited to, *Escherichia coli, Salmonella choleraesius, Listeria monocytogenes, Staphylococcus epidermidis, Staphylococcus saprophyticus, Staphylococcus aureus, Bacillus thuringiensis, Corynebacterium xerosis* and mixtures thereof. In another aspect of Applicants' invention, bacteria that can be reduced and/or whose growth is inhibited by contact with the compositions disclosed herein and/or the compound having Formulae I-V include, but are not limited to, Staphylococcus epidennidis, Staphylococcus aureus, Staphylococcus saprophyticus, Corynebacterium xerosis, Bacillus thurengiensis and mixtures thereof.

Methods of Use

Bacteria levels on a substrate, including but not limited to a substrate comprising a textile, can be reduced (i.e., rendered inactive, killed, etc.) and/or bacterial growth there on can be inhibited by contacting said substrate with the compositions and/or the compounds disclosed herein.

A bacteria-reduced or growth inhibiting substrate/article results from the practice of the method of the present invention.

Examples of substrates that may be treated according to the method of the present invention include, but are not limited to, utensils, dishes, countertops, cookware, pots, pans, skillets, baby bottles, baby nipples, glassware, dentures, kitchen cutting boards made of wood, textiles, articles comprising textiles such as fabrics, garments, and linens, sponges, brushes, plastic gloves, scouring pads, reusable wipes, animal and human skin (i.e., personal cleansing applications), and mixtures thereof. In addition to these substrates, the substrates may include food articles, such as fruits, meats and liquids, such as water.

Antibacterial Compounds

The compounds of present invention include non-halogenated nitrile-substituted salicylanilide compounds having Formulae IV and V below:

Formula IV

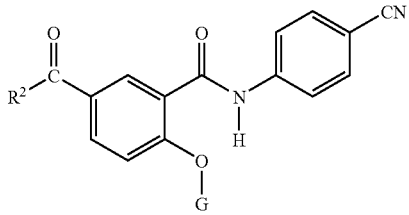

Formula V

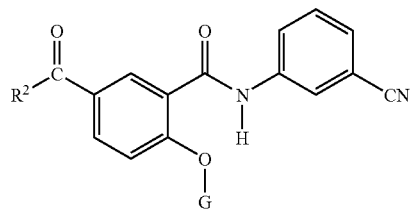

wherein $R^2$ for Formula IV and V is selected from the group consisting of:
i) H;
ii) $C_1$-$C_{16}$ linear or branched, substituted or unsubstituted alkyl;
iii) $C_2$-$C_{16}$ linear or branched, substituted or unsubstituted alkenyl;
iv) $C_2$-$C_{16}$ linear or branched, substituted or unsubstituted alkynyl;
v) $C_3$-$C_{16}$ linear or branched, substituted or unsubstituted cycloalkyl;
vi) $C_3$-$C_{16}$ linear or branched, substituted or unsubstituted cycloalkenyl;
vii) $C_7$-$C_{16}$ linear or branched, substituted or unsubstituted alkaryl;
viii) $C_7$-$C_{16}$ linear or branched, substituted or unsubstituted aralkyl;
ix) $C_6$-$C_{16}$ substituted or unsubstituted aryl; and
x) $C_5$-$C_{20}$ heteroaryl units comprising one or more heteroatoms selected from the group consisting of nitrogen, oxygen, sulfur, and mixtures thereof; and G is H, a suitable charge balancing counterion $(M^{n+})_{1/n}$, or a cleaveable group selected from the group consisting of $Si((O)_p R^3)_3$, where p is independently 0 or 1; $C(O)_q ((O)_p R^3)_r$, wherein p is independently 0 or 1 and when q is 1, r is 1, and when q is 0, r is 3; $R^3$ is independently selected from the group consisting of $C_1$-$C_{16}$ linear or branched, substituted or unsubstituted alkyl, alkenyl, alkynyl, cycloalkyl, cycloalkenyl, alkaryl, aralkyl, and aryl, and mixtures thereof.

In another aspect of the invention, $R^2$ for Formula IV and V is selected from the group consisting of $C_1$-$C_{16}$ linear or branched, substituted or unsubstituted alkyl and $C_6$-$C_{16}$ substituted or unsubstituted aryl.

In another aspect of the invention, $R^2$ for Formula IV and V is selected from the group consisting of $C_5$-$C_{11}$ linear or branched, substituted or unsubstituted alkyl and $C_6$-$C_{14}$ substituted or unsubstituted aryl.

Method of Synthesizing a 5-Acyl Substituted Salicylamide

Applicants have surprisingly found that 5-acyl substituted salicylamides may be synthesized by obtaining a salicylamide comprising an acyl group attached to the phenolic oxygen atom at position 2 of said salicylamide, and moving the attachment point of said acyl group from said phenolic oxygen atom to the carbon atom at the 5 position of said salicylamide as illustrated below.

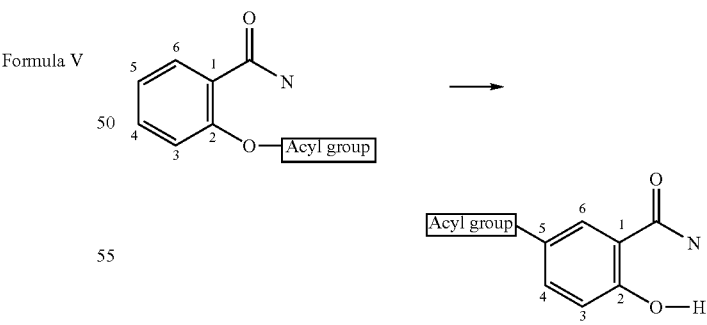

In one aspect of the method, moving said acyl group comprises the step of contacting a salicylamide comprising an acyl group attached to the phenolic oxygen atom at position 2 of said salicylamide with a Lewis acid. Suitable Lewis acids include, but are not limited to aluminum chloride, stannic chloride and boron trifluoride all of which can be obtained from Aldrich, P.O. Box 2060 Milwaukee, Wis. U.S.A. 53201.

In another aspect of the present method, said moving step is performed in the presence of a solvent. Suitable solvents include, but are not limited to carbon disulfide which can be obtained from Aldrich, P.O. Box 2060 Milwaukee, Wis. U.S.A. 53201.

The rearrangement is surprisingly found to be both chemoselective, in that the ester bond breaks in preference to the amide bond, and regioselective, in that the 5-regioisomer is obtained.

Any substituent that does not inhibit and/or modify the rearrangement of the acyl group may be covalently bound to the nitrogen atom of the salicylamide. Non-limiting examples of such substituents include, but are not limited to, H, linear or branched, substituted or unsubstituted alkyl and/or substituted or unsubstituted aryl.

The method disclosed herein, in all of its aspects, can be used to synthesize compounds having Formulae I-V. Compounds having Formulae I-V are described in detail in the present specification.

EXAMPLE I

A non-limiting synthesis example for making an antibacterial agent in accordance with the present invention is provided below.

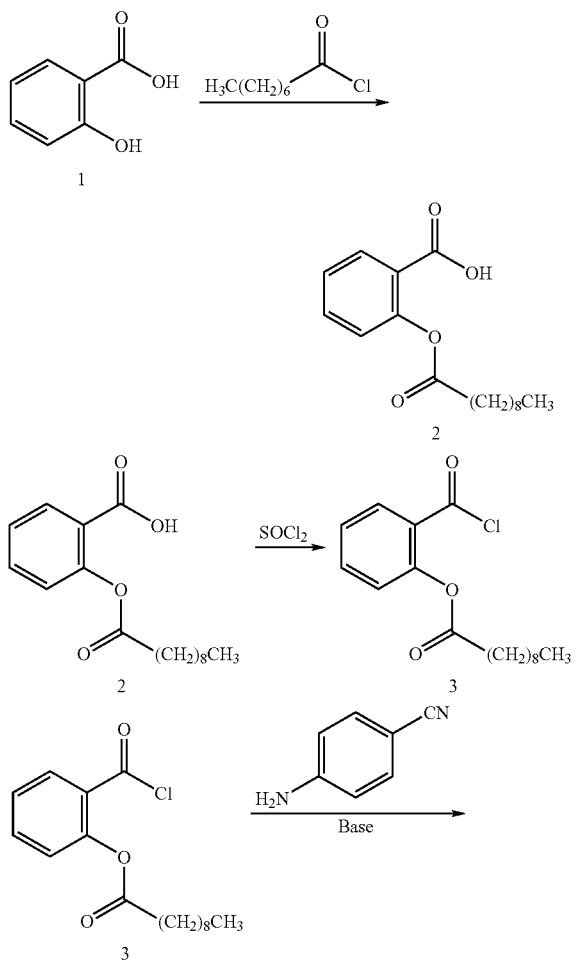

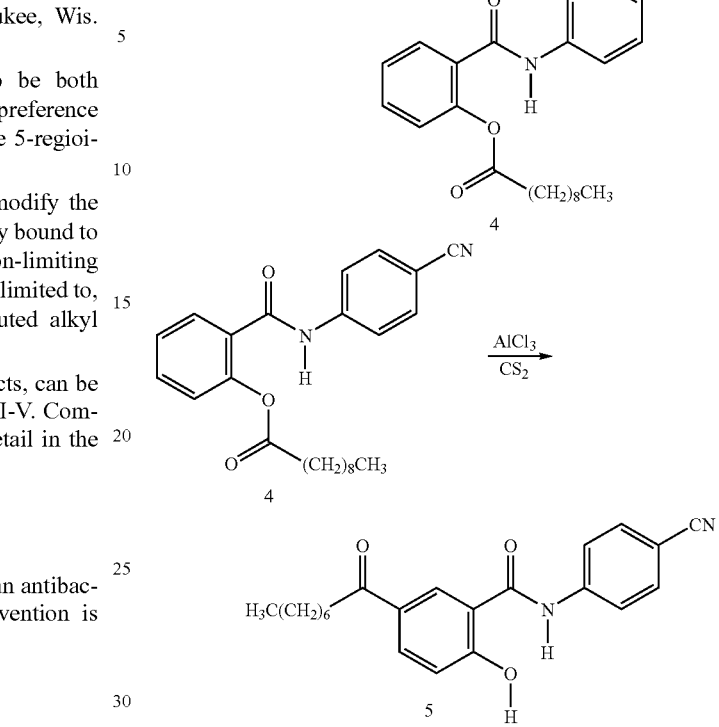

2-(Decanoyloxy)benzoic acid (2) is synthesized as follows: To a flame dried 250 mL three neck round bottomed flask equipped with an argon inlet, addition funnel, magnetic stir bar, and thermometer, is added 10.0 g of salicylic acid, 100 mL benzene, and 5.72 g pyridine. The addition funnel is charged, over a 60 minute period, with 13.81 g decanoyl chloride, while maintaining a temperature <35° C. Upon complete addition, the reaction is allowed to stir for 18 hours. The reaction is then quenched with 100 mL of 1N HCl and the organic phase is then separated, dried with sodium sulfate, filtered and the filtrate evaporated to dryness. The resulting solid is dissolved in 15 mL chloroform:formic acid (97.5:2.5) and then chromatographed on silica using the chloroform:formic acid (97.5:2.5). Yield of (2) after purification is 13.8 g.

2-(Decanoyloxy)-N-(4-cyanophenyl)-benzamide, (4) is synthesized as follows: To a flame dried 250 mL three neck round bottomed flask, equipped with an argon inlet, magnetic stir bar, oil bath, and thermometer, is added 13.5 g of 2-(decanoyloxy)benzoic acid (2) and 100 mL toluene. The resulting solution is warmed to 90° C. and 6.02 g of thionyl chloride is added, then allowed to stir for 2 hours to yield (3). Then 16.3 g of 4-cyanoanline, in 4×4 g portions, is added over 30 minutes. Once addition is complete the reaction is stirred for an additional 1 hour. Then the reaction is diluted with 150 mL water and then poured into a separatory funnel along with 500 mL chloroform and 250 mL 1N HCl. The contents of the funnel are thoroughly mixed and allowed to separate. The aqueous phase is discarded and organic phase is washed with an additional 3×250 mL 1N HCl. The organic phase is then dried with sodium sulfate, filtered, and the filtrate evaporated to dryness to produce the crude product as an oil. The oil can be further purified by column chromatography using 4:1 hexanes:ethyl acetate. Yield of (4) after purification is 9.6 g.

N-(4-Cyanophenyl)-2-hydroxy-5-(1-oxodecyl)-benzamide, (5) is synthesized as follows: To a flame dried 25 mL three neck round bottomed flask, equipped with an argon inlet, magnetic stir bar, oil bath, condenser, and thermometer, is added 1.0 g of (4) and 15 mL of carbon disulfide. To the reaction mixture is added 0.68 g of aluminum chloride and then the reaction is refluxed for 3 hours, followed by removal of the solvent. The reaction is then heated an additional 2 hours at 90° C. without solvent, followed by cooling to room temperature. The residue is treated with 10 mL water and then extracted with 50 mL ethyl acetate. The organic phase is separated, dried with sodium sulfate, filtered and the filtrate evaporated to yield (5). The product can be further purified using column chromatography (72:25 hexanes:ethylacetate) or by crystallization from benzene.

All of the aforementioned specified reagents, except (2), (3) and (4) can be obtained from Aldrich, P.O. Box 2060 Milwaukee, Wis. U.S.A. 53201.

What is claimed is:

1. A method of reducing bacteria or inhibiting bacterial growth comprising contacting a substrate comprising a textile with a compound of formula I:

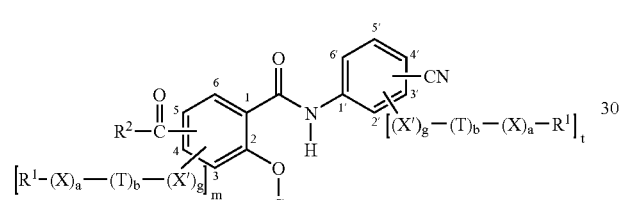

Wherein:
 a.) m is an integer from 0 to 3;
 b.) t is an integer from 0 to 4;
 c.) a is 0 or 1;
 d.) b is 0 or 1;
 e.) g is 0 or 1;
 f.) $R^1$ for said radical is independently selected from the group consisting of:
  i) H;
  ii) $C_1$-$C_{16}$ linear or branched, substituted or unsubstituted alkyl;
  iii) $C_2$-$C_{16}$ linear or branched, substituted or unsubstituted alkenyl;
  iv) $C_2$-$C_{16}$ linear or branched, substituted or unsubstituted alkynyl;
  v) $C_3$-$C_{16}$ linear or branched, substituted or unsubstituted cycloalkyl;
  vi) $C_3$-$C_{16}$ linear or branched, substituted or unsubstituted cycloalkenyl;
  vii) $C_7$-$C_{16}$ linear or branched, substituted or unsubstituted alkaryl;
  viii) $C_7$-$C_{16}$ linear or branched, substituted or unsubstituted aralkyl;
  ix) $C_6$-$C_{16}$ substituted or unsubstituted aryl;
  x) $C_5$-$C_{20}$ heteroaryl units comprising one or more heteroatoms selected from the group consisting of nitrogen, oxygen, sulfur, and mixtures thereof; and
  xi) a suitable charge balancing counterion $(M^{n+})_{1/n}$, provided a and b are both 1 and X is selected from O and S;
  xii) when a, b and g are all 0 for any single radical, $R^1$—$(X)_a$-$(T)_b$-$(X')_g$—, $R^1$ for said radical may be further selected from the group consisting of CN, an amine oxide moiety, $NO_2$ and mixtures thereof;
 g.) X and X', when present, are selected from O, S, and $NR^2$;
 h.) each $R^2$ is independently selected from the group consisting of:
  i) H;
  ii) $C_1$-$C_{16}$ linear or branched, substituted or unsubstituted alkyl;
  iii) $C_2$-$C_{16}$ linear or branched, substituted or unsubstituted alkenyl;
  iv) $C_2$-$C_{16}$ linear or branched, substituted or unsubstituted alkynyl;
  v) $C_3$-$C_{16}$ linear or branched, substituted or unsubstituted cycloalkyl;
  vi) $C_3$-$C_{16}$ linear or branched, substituted or unsubstituted cycloalkenyl;
  vii) $C_7$-$C_{16}$ linear or branched, substituted or unsubstituted alkaryl;
  viii) $C_7$-$C_{16}$ linear or branched, substituted or unsubstituted aralkyl;
  ix) $C_6$-$C_{16}$ substituted or unsubstituted aryl; and
  x) $C_5$-$C_{20}$ heteroaryl units comprising one or more heteroatoms selected from the group consisting of nitrogen, oxygen, sulfur, and mixtures thereof;
 i.) T, when present, is selected from C=O, C=S, S=O, and $SO_2$; when T is S=O or $SO_2$, X and X' associated with said T may not be S;
 j.) G is:
  i) H;
  ii) a suitable charge balancing counterion $(M^{n+})_{1/n}$, or
  iii) a cleaveable group selected from the group consisting of $Si((O)_p R^3)_3$, where p is independently 0 or 1; $C(O)_q((O)_p R^3)_r$, wherein p is independently 0 or 1 and when q is 1, r is 1, and when q is 0, r is 3; $R^3$ is independently selected from the group consisting of $C_1$-$C_{16}$ linear or branched, substituted or unsubstituted alkyl, alkenyl, alkynyl, cycloalkyl, cycloalkenyl, alkaryl, aralkyl, and aryl, and mixtures thereof provided that when, for any radical, b is 0, a, g, or a and g are 0 for said radical.

2. A substrate treated according to the method of claim 1.

3. The method of claim 1, wherein said compound is selected from:

A)
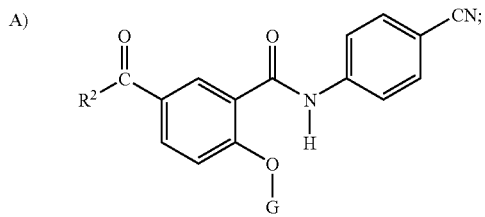

B)

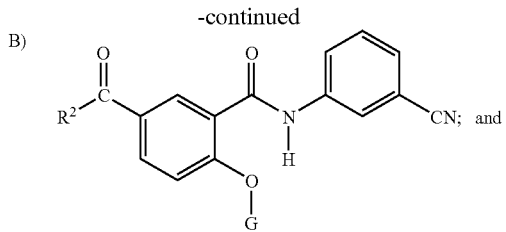

C) mixtures thereof;

wherein $R^2$ is selected from the group consisting of:
i) H;
ii) $C_1$-$C_{16}$ linear or branched, substituted or unsubstituted alkyl;
iii) $C_2$-$C_{16}$ linear or branched, substituted or unsubstituted alkenyl;
iv) $C_2$-$C_{16}$ linear or branched, substituted or unsubstituted alkynyl;
v) $C_3$-$C_{16}$ linear or branched, substituted or unsubstituted cycloalkyl;
vi) $C_3$-$C_{16}$ linear or branched, substituted or unsubstituted cycloalkenyl;
vii) $C_7$-$C_{16}$ linear or branched, substituted or unsubstituted alkaryl;
viii) $C_7$-$C_{16}$ linear or branched, substituted or unsubstituted aralkyl;
ix) $C_6$-$C_{16}$ substituted or unsubstituted aryl; and
x) $C_5$-$C_{20}$ heteroaryl units comprising one or more heteroatoms selected from the group consisting of nitrogen, oxygen, sulfur, and mixtures thereof; and G is H, a suitable charge balancing counterion $(M^{n+})_{1/n}$, or a cleaveable group selected from the group consisting of $Si((O)_p R^3)_3$, where p is independently 0 or 1; $C(O)_q((O)_p R^3)_r$, wherein p is independently 0 or 1 and when q is 1, r is 1, and when q is 0, r is 3; $R^3$ is independently selected from the group consisting of $C_1$-$C_{16}$ linear or branched, substituted or unsubstituted alkyl, alkenyl, alkynyl, cycloalkyl, cycloalkenyl, alkaryl, aralkyl, and aryl, and mixtures thereof.

4. The method of claim 3 wherein for said compound $R^2$ is selected from the group consisting of:
a.) $C_1$-$C_{16}$ linear or branched; substituted or unsubstituted alkyl; and
b.) $C_6$-$C_{16}$ substituted or unsubstituted aryl.

5. The method of claim 4 wherein for said compound $R^2$ is selected from the group consisting of:
a.) $C_5$-$C_{11}$ linear or branched, substituted or unsubstituted alkyl; and
b.) $C_6$-$C_{14}$ substituted or unsubstituted aryl.

* * * * *